United States Patent [19]

Ueno et al.

[11] 4,045,551

[45] Aug. 30, 1977

[54] SUBLIMABLE AROMATIC COMPOSITIONS

[75] Inventors: Yasuhiko Ueno, Kawanishi; Yoshito Saeki, Suita; Takuya Akiyama, Nagaokakyo; Masao Fujita, Amagasaki, all of Japan

[73] Assignee: Ogawa & Co., Ltd., Osaka, Japan

[21] Appl. No.: 592,531

[22] Filed: July 2, 1975

Related U.S. Application Data

[63] Continuation-in-part of Ser. No. 424,313, Dec. 13, 1973, abandoned.

[30] Foreign Application Priority Data

Jan. 19, 1973  Japan ................................. 48-9362
July 11, 1973  Japan ................................ 48-66508

[51] Int. Cl.$^2$ ..................... A61K 7/46; A61L 13/00; A01N 17/02
[52] U.S. Cl. ................................. 424/76; 252/522; 424/278; 424/311; 424/312; 424/317; 424/333; 424/340; 424/343; 424/346; 424/350; 424/358
[58] Field of Search ..................... 424/76, 278, 358; 252/522

[56] References Cited

U.S. PATENT DOCUMENTS

| 850,849 | 4/1907 | Power | 424/76 X |
|---|---|---|---|
| 1,063,313 | 6/1913 | Anders | 424/76 X |
| 1,346,337 | 7/1920 | Roark | 424/76 |
| 2,905,591 | 9/1959 | Bulloff | 424/76 |
| 3,639,630 | 2/1972 | Sander et al. | 424/278 X |
| 3,644,646 | 2/1972 | Sander et al. | 424/278 X |

OTHER PUBLICATIONS

Chem. Abst., Ohshiro et al., vol. 68 (1968) 48981b.
Chem. Abst., Tishchenko, vol. 59 (1963) pp. 429-430.
Chem. Abst. 7th Coll. Index, vols. 56-65 (1962-1966) p. 23, 362s.

*Primary Examiner*—Allen J. Robinson
*Attorney, Agent, or Firm*—Wenderoth, Lind & Ponack

[57] ABSTRACT

Sublimable aromatic compositions containing triisopropyl-s-trioxane or tritertiary-butyl-s-trioxane and an additive such as perfume, which compositions, contrary to conventional sublimable materials, are characterized by their ability to contain large percentages of perfume without a drop in their melting point, enabling manufacture of superfine sublimable aromatic compositions.

8 Claims, No Drawings

SUBLIMABLE AROMATIC COMPOSITIONS

This is a continuation-in-part of Serial No. 424,313, filed Dec. 13, 1973, now abandoned.

The present invention relates to sublimable aromatic compositions and their preparation and use. It relates to sublimable aromatic compositions comprising sublimable materials far more advantageous in sublimability, aromatizability and melting point than conventional materials of this kind.

Conventionally, various kinds of sublimable aromatic compositions have been manufactured by means of mixing non-sublimable materials such as perfume, coloring material, pigment, deodorant, and the like, or combinations thereof, with sublimable materials such as camphor, naphthalene, p-dichlorobenzene and the like, or combinations thereof, to prepare room aromatics, toilet room deodorants, insecticides, animal repellents, telephone receiver aromatics and the like.

These conventional sublimable materials, however, are defective in such regards as being objectionably odorous themselves, and being liable to melt in proportion to the amount of perfume contained therein, their melting point decreasing significantly in the presence of more than a minimal amount of perfume. For instance, when p-dichlorobenzene is the sublimable material, only up to 1% by weight of perfume may be mixed therewith in regard to the foregoing effect.

The present invention obviates the foregoing defects by using two trioxane homologues, triisopropyl-s-trioxane and tritertiary-butyl-s-trioxane, which two substances have been confirmed to be quite suitable for preparing sublimable aromatic composites by mixing them with non-sublimable materials. [These two substances will be referred to hereinafter as trioxane (1) and trioxane (2), respectively.]

The present invention resulted from a thorough study of trioxanes (1) and (2) in a series of tests confirming said materials to be of sublimable, odorless character, capable of admixture with a large volume of perfume oil without a drop in their melting points. The experiments have proven that trioxane, shown by the general formula below, is readily sublimed, but is odorous when R = H, is an odorous liquid when R = methyl or ethyl, and only when R = isopropyl or tertiary-butyl, is it an odorless, sublimable crystal. As the result, the trioxanes (1) and (2), synthesized by means of cyclizing and trimerizing corresponding aldehydes by mineral acids, halogens, $ZnCl_2$, $PCl_5$, and the like, have been found to be capable of obviating the defects of conventional sublimable materials, with the melting point being graduated at 62.5° C in the case of trioxane (1) and 92.0° C in the case of trioxane (2).

Formula of Trioxane:

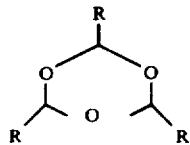

The odorless character of trioxanes (1) and (2) enables them to be applicable to any kind of aromatic, showing their extent of use to be wider than conventional sublimable materials. Furthermore, trioxanes (1) and (2) are chemically stable, free from influence, such as decomposing effect, of other chemicals, and have no influence against additives thereto.

The sublimable character of said materials was shown as follows:

The trioxanes (1) and (2), each molded into a disc tablet 3.0 cm in diameter and 0.23 cm thick, were left in a thermostat at variable temperatures while maintaining the humidity at 65% ± 5% for seven days, their sublimation percentages being recorded as below (Table I), proving that said materials are quite suitable for the manufacture of sublimable aromatic compositions.

Table I

| Temperature (° C) | (1) (%) | (2) (%) |
|---|---|---|
| 20 ± 1 | 42.2 | 16.9 |
| 30 ± 1 | 73.3 | 29.3 |
| 37 ± 1 | 98.8 | 39.5 |

As described heretofore, conventional sublimable materials, being objectionably odorous themselves, make it necessary to have a large content of perfume to cover their odors with fragrance, which is inconsistent with their inability to contain such large amounts of perfume because of the large drop in their melting point; the permissible content of perfume ranging only from 0.5% to 1.0% in the case of using p-dichlorobenzene as the sublimable material.

As a countermeasure, polyvinylalcohol, CMC, cellulose, diatomaceous earth, and the like (refer to Japan Patent Publication No. 47-29536) or gelling agent have been used, the former as additives to the foregoing sublimable materials, both providing a solution to the problem of drop in melting point. They, however, have proven to be defective in the state of prepared compositions, i.e., said additives remain unsublimed in case of using the former and become deformed or dwindle in size in case of using the gelling agent.

Compared to above described sublimable materials, trioxanes (1) and (2) are odorless, sublimable and exhibit a very small drop in melting point; that is, the melting point never drops below 50° C even in the presence of 15% of perfume in the case of trioxane (1), or below 65° C in the presence of 20% perfume in the case of trioxane (2). This enables one to decide the amount of perfume and other additives as required in accordance with the purpose of producing the composition to be used.

To described more concretely, Jasmin OG - 100 (produced by Ogawa & Co., Ltd.) was added to trioxanes (1) and (2) at random in various mixing ratios, the mixture being heated until becoming a solution, said solution then being cooled. The relation between the perfume content and melting point of trioxanes (1) and (2) was disclosed as the result, which is shown in comparison with that of p-dichlorobenzene in Table II.

As seen in Table II, trioxane (1) is able to contain perfume up to 10 - 15%; trioxane (2) up to 15 - 20%.

In the case of trioxane (1), the composition of the present invention preferably contains 80 - 99% by weight of trioxane (1) and 1 - 20% by weight of the additive, which additive contains at least one of, for example, a perfume, a deodorant and an insecticide. In the case of trioxane (2), the composition of the present invention preferably contains 75 - 99% by weight of trioxane (2) and 1 - 25% by weight of the additive, which additive contains at least one of, for example, a perfume, a deodorant and an insecticide.

The following examples serve to illustrate the present invention, which examples are not, however, limitive of the present invention.

EXAMPLE I

Sulfuric acid, 50% in concentration, and 50 parts (parts denote weight-parts hereinunder) by weight thereof, was cooled down to 0° C – 3° C, adding thereto 15 parts of isobutylaldehyde dropwise under agitation for one hour. 30 minutes later, 30 parts of petroleum ether was added thereto to extract crystals separated therefrom. The petroleum ether layer was separated and washed with 5% sodium bicarbonate solution and then washed with water until said layer was neutral. The organic layer was dried over anhydrous magnesium sulphate and then filtered to recover the petroleum ether. The residue was cooled, obtaining 10 parts of solid raw triisopropyl-s-trioxane, which was recrystallized from methanol to obtain 9.5 parts of pure, odorless product having a melting point of 62.5° C. The product proved to be equivalent to the standard compound, based on IR and NMR spectra.

Further experiments using said crystals were conducted as follows:

EXAMPLE II

To 100 parts of triisopropyl-s-trioxane was added 10 parts of perfume (Jasmin OG – 100 of Ogawa & Co., Ltd.) under thorough mixing, the resultant mixture being punched into tablets. Said tablets proved to be of sublimable aromatic composite nature usable for room deodorization.

EXAMPLE III

To 5.0 grams of purified triisopropyl-s-trioxane was added 0.5 gram of perfume (Rose OG – 100 of Ogawa & Co., Ltd.) under thorough mixing, the mixture obtained thereby being converted to disc tablets 3.0 cm in diameter and 0.76 cm in thickness. The tablets showed no sign of melting or deformation during storage in a thermostat keeping the temperature at 50° C ± 1° C for a lengthy period of time. The tablets were effective enough to generate pleasing fragrance in a room 26.28 cubic meters in capacity.

For comparison, an experiment was carried out using, as substrate, p-dichlorobenzene in lieu of triisopropyl-s-trioxane. As in the foregoing Examples, 0.5 g of perfume (Rose OG – 100 produced by Ogawa & Co., Ltd.) was first admixed with 5.0 g of p-dichlorobenzene. The resultant mixture was liquid at 50° C ± 1° C, and was found unpracticable.

EXAMPLE IV

To 100 parts of purified triisopropyl-s-trioxane was added 10 parts of deodorant (Cleaner OG – 1000 of Ogawa & Co., Ltd.) under thorough mixing, resulting in the production of sublimable aromatic tablets in various shapes for commercial use.

EXAMPLE V

To 3.0 grams of purified triisopropyl-s-trioxane was added to 0.45 gram of deodorant (Cleaner OG – 2000 of Ogawa & Co., Ltd.) under thorough mixing, the mixture thereby being molded into tablets of sublimable aromatic deodorant 3.0 cm in diameter and 0.47 cm thick. This product was set in a flush toilet room on a wall wherein at a point one meter above the floor, the room measuring 0.8 meter wide at the entrance, 1.15 meters deep, and 2.38 meters high, and was left there in temperatures ranging from 8° C to 12° C for 20 days, with a panel of 10 testers standing by in turn to observe the odorous condition of the room through the entire period. The testers unanimously agreed as to the effectiveness of the product as being able to fill the room with a pleasant fragrance.

EXAMPLE VI

To 20 parts of trimethyl acetaldehyde was added dropwise under stirring 100 parts of 70% sulphuric acid at temperatures ranging from 5° C to 10° C for 2 hours. The resultant mixture was left standing for an additional one hour, and then 60 parts of petroleum ether was added thereto, resulting in the extraction of separated crystals. After the petroleum ether layer was separated, the mixture was neutralized with a sodium carbonate aqueous solution, then dried by anhydrous magnesium sulphate. After filtering, the petroleum ether was recovered therefrom, leaving 13 parts of raw crystals. By subjecting the raw crystals to recrystalization with methanol, 12 parts of pure white and odorless sublimable crystals were obtained. The product, having a melting point of 92° C, proved to be quite identical to pure tritertiary-butyl-s-trioxane based on IR, NMR and Mass Spectra. Further experiments were carried out with the use of this material.

EXAMPLE VII

To 20 grams of purified tritertiary-butyl-s-trioxane was added 2 grams of perfume (Cologne OG – 400 of Ogawa & Co., Ltd.) under thorough mixing. The mixture was formed into a disc tablet 6.0 cm in diameter and 0.8 cm in thickness. The tablet was stored in a thermostat at 60° C ± 1° C for a lengthy period of time without showing any sign of melting or formation. The tablet was effective enough to generate a pleasant fragrance in a room of 26.2 cubic meters.

EXAMPLE VIII

To 100 parts of purified tritertiary-butyl-s-trioxane was added 15 parts of deodorant (Deodorant OG – 1000 of Ogawa & Co., Ltd.) under thorough mixing. The mixture was molded into a toilet deodorant high in melting point and rich in pleasant odor by applying a blend-melt-solidifying process to the tablet.

EXAMPLE IX

To 0.5 gram of purified triteriary-butyl-s-trioxane was added 0.75 gram of aromatic deodorant (Freshner OG – 400 of Ogawa & Co., Ltd.) under thorough mixing. The mixture was molded into a disc tablet 3.0 cm in diameter and 0.78 cm in thickness. The tablet was put on a wall one meter above the floor in a toilet room measuring 1 meter long, 2.38 meters high and 0.8 meter wide maintained at a temperature of 15° C – 25° C for 20 days. A panel of 10 testers stood by in turn to observe the odorous condition in the room, unanimously agreeing to the effectiveness of the tablet in filling the room with a pleasant fragrance through the entire testing period.

EXAMPLE X

To 3.0 grams of triisopropyl-s-trioxane was added 0.2 gram each of linalool, linalool oxide, anethol, cinnamic aldehyde, cinnamon oil, menthol, menthylacetate, eugenol and thymol, respectively, under thorough mixing. Each of the mixtures was punched into a disc tablet 3.0 cm in diameter and 0.47 cm thick, all alike.

Twenty heads of 50-day old larvae of Tinae pellionella weighing 4.5 mg per head on the average, fed at a temperature of 20° C ± 1° C and humidity of 65% ± 5%, were put in a Petri dish with flakes of 500 mg dried bonito, with a stainless wire net of 80 meshes separating the dish proper with its cover to permit the larvae to breath. The tablets were arranged separately from each other at the center of the dish, the dish measuring 8.5 cm in inside diameter. As the result of the test, continued at a temperature of 20° C ± 1° C and humidity of 65% ± 5% for 20 days, the effect of the tablets in driving out the insects was recorded as shown in Table III. The tablets not only showed a remarkable effect for killing or reducing the weight of the insects but also proved to be quite free from melting and deformation.

EXAMPLE XI

Floral perfume (Perfume OG – 401 of Ogawa & Co., Ltd.) was mixed with triisopropyl-s-trioxane dividedly in three mixing ratios, namely, 3%, 5% and 10%. 3 grams of each mixture was molded into a disc tablet 3 cm in diameter, respectively. The effect of the tablets in driving out the insects was determined in a manner similar to that described in Example X, except that the larvae were fed with 500 mg of white pure wool which has no mothproof character. The test results, as shown in Table IV shows that the sublimable aromatic tablets have a strong effect for killing insects.

Table V

| Chemicals | Quantity (%) |
|---|---|
| Terpinol | 1.50 |
| Phenylacetate | 0.20 |
| Cinnamic Acid | 0.20 |
| Eugenol | 0.05 |
| Thymol | 0.05 |
| Phenoxyethyl Alcohol | 3.00 |
| Perfume (Floral 100 of Ogawa & Co., Ltd.) | 5.00 |
| Triisopropyl-s-trioxane | 90.00 |
| TOTAL | 100.00 |

A composition was prepared by mixing the chemicals, as shown in Table V, and 2.5 g of the composition was molded into a ring-shaped tablet 4.0 cm in outside diameter and 2.0 cm in inside diameter. The tablet proved to be effective as a sublimable aromatic sterilizer for telephone receivers in a test conducted in a room at 20° C for 30 days. No sign of melting, deformation or generation of objectionable odor was observed with the tablet through the entire experiment.

Any perfume, deodorant or insecticide can be used in the composition of the present invention, as long as it is liquid or solid at room temperature.

The tradename materials referred to above are defined as follows:

| Jasmin OG-100 | % by weight |
|---|---|
| Benzyl Acetate | 52.5 |
| Jasmin Absolute | 7.5 |
| α-Amylcinnamic Aldehyde | 5.6 |
| Indole | 0.2 |
| Linalool | 6.7 |
| Benzyl Alcohol | 7.5 |
| Benzyl Butyrate | 4.7 |
| Cananga Oil | 0.8 |
| Orange Oil Bitter | 3.8 |
| Linalyl Acetate | 4.7 |
| Methyl Anthranilate | 6.0 |
| TOTAL | 100.0 |

| Cleaner OG-1000 | % by weight |
|---|---|
| Terpineol | 28.0 |
| Hydroxycitronellal | 32.0 |
| Heliotropin | 8.0 |
| Linalool | 4.0 |
| Phenylethyl Alcohol | 8.0 |
| Phenylacetaldehyde | 0.2 |
| Anis Aldehyde | 0.4 |
| Benzyl Acetate | 7.0 |
| Cinnamyl Alcohol | 1.0 |
| Ylang - Ylang Oil | 0.8 |
| Geranyl Crotonate | 10.6 |
| TOTAL | 100.0 |

| Cologne OG-400 | % by weight |
|---|---|
| Bergamol Oil | 33.0 |
| Lemon Oil | 17.0 |
| Orange Oil Sweet | 10.0 |
| Neroli Oil | 17.0 |
| Lavender Oil | 12.0 |
| Rosemary Oil | 11.0 |
| TOTAL | 100.0 |

| Freshner OG-400 | % by weight |
|---|---|
| Phenylethyl Alcohol | 28.0 |
| Rose Oil | 6.0 |
| Ionone Alpha | 1.0 |
| Linalool | 6.0 |
| Citronellol | 17.0 |
| Rhodinol | 28.0 |
| Nonyl Aldehyde | 1.0 |
| Hydroxycitronellal | 3.0 |
| Geranyl Crotonate | 10.0 |
| TOTAL | 100.0 |

| Floral 100 | % by weight |
|---|---|
| Methyl Ionone | 16.5 |
| Ionone 100% | 51.0 |
| Orris Concrete | 5.0 |
| Cassia Absolute | 1.0 |
| Heliotropin | 6.5 |
| Bergamot Oil | 3.0 |
| Violet Leaf Absolute | 8.0 |
| Methyl Heptine Carbonate | 1.0 |
| Anis Aldehyde | 8.0 |
| TOTAL | 100.0 |

| Rose OG-100 | % by weight |
|---|---|
| Phenylethyl Alcohol | 9.0 |
| Geraniol | 40.0 |
| Rose Oil | 10.0 |
| Ionone Alpha | 4.0 |
| Linalool | 1.5 |
| Geranyl Acetate | 3.5 |
| Geranium Oil Terpeneless | 6.0 |
| Eugenol | 1.0 |
| Nonyl Aldehyde | 0.1 |
| Nerol | 20.0 |
| Orris Oil Liquid | 1.0 |
| Rhodinyl Formate | 2.0 |
| Musk Ketone | 0.8 |
| Undecylic Aldehyde | 0.2 |
| Lauric Aldehyde | 0.2 |
| Vanillin | 0.7 |
| TOTAL | 100.0 |

| Cleaner OG-2000 | % by weight |
|---|---|
| Heliotropin | 20.0 |
| Terpineol | 14.0 |
| Hydroxycitronellal | 4.0 |
| Phenylethyl Acetate | 2.0 |
| α-Amylcinnamic Aldehyde | 10.0 |
| Ionone Alpha | 2.0 |
| Cinnamyl Alcohol | 7.5 |
| Anisyl Alcohol | 10.0 |
| Isobutyl Benzoate | 14.0 |
| Lauryl Methacrylate | 6.0 |
| Geranyl Crotonate | 3.5 |
| Benzylidene Acetone | 5.0 |
| Phenylacetaldehyde | 2.0 |
| TOTAL | 100.0 |

| Deodorant OG-1000 | % by weight |
|---|---|
| Phenylacetaldehyde | 20.0 |
| Cinnamyl Alcohol | 25.0 |
| Benzyl Acetate | 5.0 |
| Heliotropin | 10.0 |
| Ionone Alpha | 2.0 |
| Coumarin | 2.0 |
| Bergamot Oil | 7.0 |
| Ylang - Ylang Oil | 2.0 |
| Terpineol | 15.0 |
| Hydroxycinnamyl Alcohol | 4.0 |
| Geranyl Crotonate | 8.0 |
| TOTAL | 100.0 |

| Perfume OG-401 | % by weight |
|---|---|
| Linalool | 15.0 |

-continued

| | |
|---|---|
| Linalool Oxide | 10.0 |
| Cinnamon Oil | 1.0 |
| Menthyl Acetate | 5.0 |
| Anethol | 3.0 |
| Jasmin Absolute | 2.0 |
| Anisaldehyde | 9.0 |
| Benzyl Acetate | 40.0 |
| α-amylcinnamic Aldehyde | 5.0 |
| Phenylethyl Alcohol | 10.0 |
| TOTAL | 100.0 |

Table II

| perfume content (Weight %) materials | 0 | 0.5 | 1 | 2 | 5 | 8 | 10 | 15 | 20 |
|---|---|---|---|---|---|---|---|---|---|
| (1) M.P. °C | 62.5 | | 61.0 −62.0 | 58.0 −60.0 | 56.0 −58.5 | 54.0 −57.0 | 52.5 −55.5 | 51.0 −54.0 | |
| (2) M.P. °C | 92.0 | | | 87.5 −90.0 | 82.0 −87.0 | | 71.0 −80.0 | 68.5 −78.0 | 66.0 −76.0 |
| p-dichloro-benzene | 53.0 | 49.0 −51.0 | 45.0 −47.0 | 38.0 −42.0 | | | | | |

Table III

| | at the end of 20 - days testing period | | | | |
|---|---|---|---|---|---|
| chemicals | sublimation rate of tablet (%) | feeding attack (mg.) | feeding attack rate (%) | weight change of twenty Tinea Pellionella (mg) | no. of killed Tinea Pellionella/20 heads |
| linalool | 12.5 | 0 | 0 | −47.2 | 20 |
| linalool oxide | 11.2 | 20.6 | 4.1 | −45.9 | 17 |
| anethol | 12.2 | 3.0 | 0.6 | −47.6 | 20 |
| cinnamic aldehyde | 12.3 | 4.5 | 0.9 | −35.8 | 20 |
| cinnamon oil | 10.8 | 6.2 | 1.2 | −24.6 | 20 |
| menthol | 11.8 | 82.6 | 16.5 | − 8.2 | 19 |
| menthyl acetate | 12.1 | 13.1 | 2.6 | −45.6 | 20 |
| eugenol | 12.6 | 5.2 | 1.4 | −46.0 | 20 |
| thymol | 12.3 | 4.1 | 0.8 | −48.5 | 20 |
| control (triisopropyl-s-trioxane only) | 7.6 | 325.0 | 65.0 | +58.2 | 0 |
| control (no chemicals) | — | 302.9 | 60.6 | +54.2 | 0 |

Table IV

| content of Perfume OG - 401 (%) | No. of Tinea Pellionella killed/ 20 heads | | | feeding attack quantity (mg) | feeding attack rate (%) |
|---|---|---|---|---|---|
| | after six days | after fifteen days | after twenty-three days | after twenty-three days | after twenty-three days |
| 0.0 (control) | 0 head | 0 head | 0 head | 251.0 | 50.2 |
| 3.0 | 3 head | 15 head | 20 head | 15.0 | 3.0 |
| 5.0 | 6 head | 20 head | 20 head | 3.5 | 0.7 |
| 10.0 | 12 head | 20 head | 20 head | 1.2 | 0.2 |

We claim:

1. An aromatic, solid, sublimable composition consisting of 80-99% by weight of triisopropyl-s-trioxane and 1-20% by weight of an additive selected from the group consisting of a perfume which is liquid at room temperature, a perfume which is solid at room temperature, a deodorant which is liquid at room temperature, a deodorant which is solid at room temperature, an insecticide which is liquid at room temperature, an insecticide which is solid at room temperature and a mixture thereof.

2. The composition according to claim 1, wherein the additive is a perfume.

3. The composition according to claim 1, wherein the additive is a deodorant.

4. The composition according to claim 1, wherein the additive is an insecticide.

5. An aromatic, solid, sublimable composition consisting of 75-99% by weight of tritertiary-butyl-s-trioxane and 1-25% by weight of an additive selected from the group consisting of a perfume which is liquid at room temperature, a perfume which is solid at room temperature, a deodorant which is liquid at room temperature, a deodorant which is solid at room temperature, an insecticide which is liquid at room temperature, an insecticide which is solid at room temperature, and a mixture thereof.

6. The composition according to claim 5, wherein the additive is a perfume.

7. The composition according to claim 5, wherein the additive is a deodorant.

8. The composition according to claim 5, wherein the additive is an insecticide.